(12) United States Patent
Gardosi

(10) Patent No.: US 6,186,945 B1
(45) Date of Patent: *Feb. 13, 2001

(54) ELONGATE FETAL PROBE WITH EXPANDABLE MEANS ON DISTAL END

(75) Inventor: Jason Otto Gardosi, Bramcote Hill (GB)

(73) Assignee: Mallinckrodt Inc., Hazelwood, MO (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

This patent is subject to a terminal disclaimer.

(21) Appl. No.: 08/839,413

(22) Filed: Apr. 14, 1997

Related U.S. Application Data

(63) Continuation of application No. 08/420,908, filed on Apr. 11, 1995, now Pat. No. 5,634,459, and a continuation of application No. 08/260,676, filed on Jun. 16, 1994, now abandoned, and a continuation of application No. 07/853,698, filed on Jun. 22, 1992, now abandoned.

(30) Foreign Application Priority Data

Nov. 28, 1989 (GB) .................................................. 8926908
Nov. 7, 1990 (WO) .................................. PCT/GB90/01708

(51) Int. Cl.[7] ...................................................... A61B 5/00
(52) U.S. Cl. ........................... 600/338; 600/339; 600/376
(58) Field of Search ................................... 600/313, 322, 600/323, 325, 327, 338, 339, 341, 351, 373, 376, 511

(56) References Cited

U.S. PATENT DOCUMENTS

| | | | |
|---|---|---|---|
| 3,326,207 | * 6/1967 | Egan | 600/376 |
| 4,270,541 | 6/1981 | Okamoto et al. | 128/344 |
| 4,338,943 | 7/1982 | Okamoto et al. | 128/344 |
| 4,543,965 | 10/1985 | Pack et al. | 128/748 |
| 4,693,704 | 9/1987 | Ogita | 604/55 |
| 4,776,349 | 10/1988 | Nashef et al. | 128/786 |
| 4,873,986 | 10/1989 | Wallace | 128/670 |
| 4,938,218 | * 7/1990 | Goodman et al. | 600/338 |
| 4,976,692 | 12/1990 | Atad | 604/101 |
| 5,247,932 | * 9/1993 | Chung et al. | 600/338 |
| 5,634,459 | * 6/1997 | Gardosi | 600/376 |

FOREIGN PATENT DOCUMENTS

| | | |
|---|---|---|
| 645 765 | 1/1936 | (DE) . |
| 0 097 454 A2 | 1/1984 | (EP) . |
| 0 121 571 A1 | 10/1984 | (EP) . |
| 0 377 749 A1 | 7/1990 | (EP) . |
| WO 83/03189 | 9/1983 | (WO) . |
| WO 88/02616 | 4/1988 | (WO) . |

* cited by examiner

*Primary Examiner*—Linda C. M. Dvorak
*Assistant Examiner*—Bryan K. Yarnell
(74) *Attorney, Agent, or Firm*—Townsend and Townsend and Crew LLP

(57) ABSTRACT

A fetal probe with an elongate body and fetal sensor for insertion above the presenting part of the fetus. An expandable means is on the distal end of the body of the sensor for urging the sensor into engagement with the fetus. The expandable means has a collapsed state to facilitate insertion into the cervix.

5 Claims, 3 Drawing Sheets

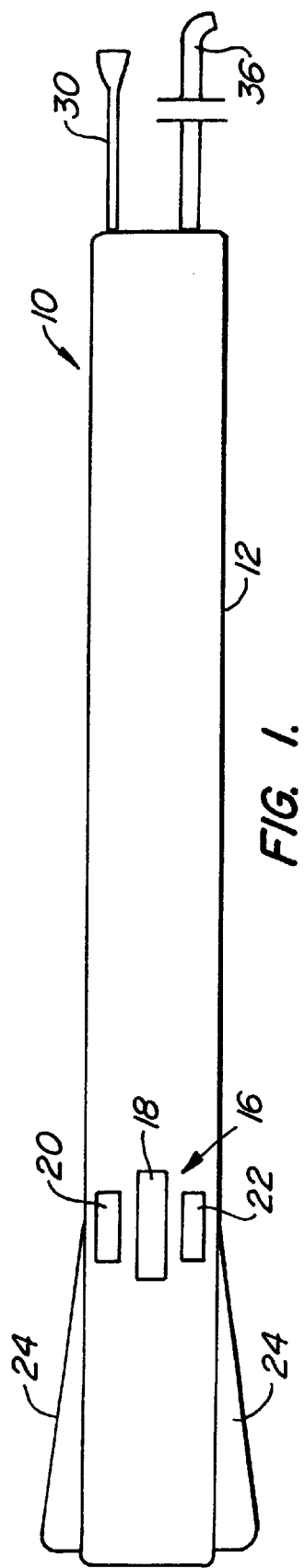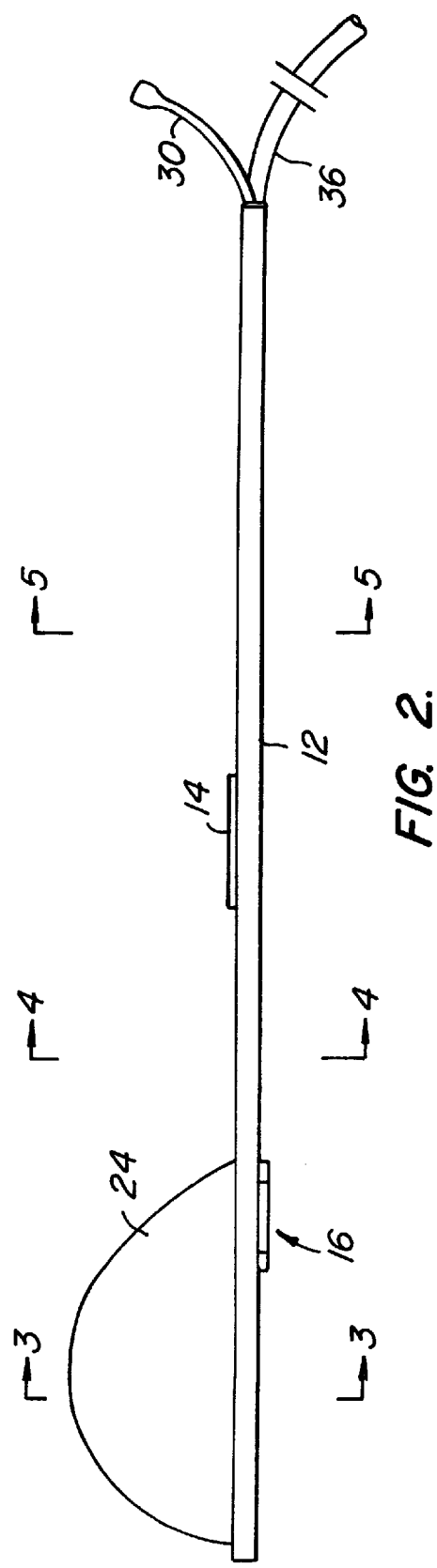

ELONGATE FETAL PROBE WITH EXPANDABLE MEANS ON DISTAL END

This application is a continuation of Ser. No. 08/420,908, filed Apr. 11, 1995, now U.S. Pat. No. 5,634,459; and a continuation of Ser. No. 08/260,676, filed Jun. 16, 1994, which is now abandoned, and a continuation of Ser. No. 07/853,698, filed Jun. 22, 1992, which is now abandoned.

This invention relates to obstetrics and in particular to probes for fetal monitoring.

BACKGROUND OF THE INVENTION

The monitoring of the fetus is a vital aspect of modern labour management. Assessment of the fetal heart rate is a mainstay of such monitoring and can be done externally or by internal electrodes. In certain circumstances, internal monitoring is preferred and provides a more accurate representation of the fetal heart rate pattern for analysis. Internal monitoring probes are usually made of arcuate or spiral metal needles which perforate the scalp skin and are thus secured to obtain electrical signals from the fetal heart. Such probes can be considered invasive to the fetus.

Alternatively, intrauterine probes have been designed which do not have to perforate the fetal skin and which have contact electrodes that lie apposed to the surface of the fetal body and scalp. Reference is directed for example to U.S. Pat. No. 3,326,207 and GB-A-2,195,877. These probes are long and have several built-in electrodes to ensure that at least one of them is in sufficient contact with the fetal skin to obtain an adequate signal. Another sensor, some distance away, is used as a reference electrode. Unless already ruptured spontaneously, the membranes of the amniotic sac have to be ruptured artificially before such a probe is inserted. Because of this aspect and its overall length, such probes can be considered invasive to the mother and the uterine environment of the fetus.

The probe disclosed in GB-A-2,195,877 comprises an elongate flexible strip having a series of protruding electrodes. The strip is of sufficient length (approximately 50 cm) to extend past the fetal head and along the trunk of the fetus. U.S. Pat. No. 3,328,207, issued in 1967, proposed a fetal probe having two inflatable balloons positioned as to contact the shoulder and hip/thigh regions of the fetus, respectively. Each balloon is spherical and carries six or so equatorially spaced electrodes. Additionally, each electrode is provided with a port for the local discharge of a conductive solution. The construction and operation of this probe is considered to be far too elaborate and cumbersome for practical application.

SUMMARY OF THE INVENTION

It is object to this invention to provide and improved fetal probe which is not invasive to the mother or the fetus.

Accordingly, the present invention consists in one aspect in a fetal probe comprising an elongate body portion adapted for insertion into the cervix around the presenting part of the fetus, the body portion carrying fetal sensor means; characterised in that the body portion is insertable into the cervix to a length of between 10 and 20 cm and preferably about 15 cms enabling positioning of the probe such that the sensor is held against the fetal presenting part by the pressure of maternal tissue with the amniotic membrane intact.

The probe according to this invention can be inserted through the vagina into a cervical opening of 1 cm or more dilatation, with the most distal part of the probe extending into the lower part of the uterus only, inside the cervix and just above the presenting part. The amniotic membranes do not necessarily have to be ruptured to enable this insertion.

The probe can be a vehicle for a variety of monitoring functions, and the probe sensor means can take a variety of forms. Principally, the sensor means would comprise a contact electrode for obtaining the fetal heart rate signal, using a second, reference electrode positioned on the maternal surface of the near end of the probe, to be in contact with vaginal tissue. In addition, the probe can contain the sensors (photodiode and light emitting diodes (LED's)) for transcutaneous pulse oximetry. Other sensors can also be built in to measure other parameters. It has been found that most sensors can detect a satisfactory signal through intact amniotic membranes.

According to this invention, the probe can be held in place by the pressure of maternal tissues (cervix, vagina) against the fetal presenting part; but additionally it can also be secured non-invasively by an inflatable semi-cuff or balloon at the distal end of the probe. This balloon can be made of a thin plastic or synthetic-rubber material and is confined to the maternal surface of the probe. Therefore inflation will result in the fetal surface of the probe being apposed to the fetal skin, thus ensuring good contact for the built-in sensors which are located nearby. The inflated balloon also stops the probe from slipping out of the cervix and vagina during maternal movement, contractions and fetal descent, until such time that the fetal presenting part is delivered or the balloon is deflated for probe removal. As the balloon is above the presenting part, it does not interfere with its descent during labour.

Another advantage of the balloon at the distal end of the probe is that after probe insertion and balloon inflation, gentle traction on the probe will reliably find a point of optimal contact between the main sensor area of the probe and the skin of the presenting part.

According to another feature of this invention, there are one or more channels running the whole length of the probe which can be used for access into the uterus around the presenting part, without the need for an additional vaginal examination.

One beneficial use for such an access channel is for rupturing the amniotic membranes by inserting a special canula to apply localised suction or contact-glue before rupturing the membranes by traction; alternatively a small hooked or sharp-tipped flexible trochar can be inserted to perforate the membranes. Rupturing the membranes in this area above the presenting part, i.e. the 'breaking the hindwaters', is already done occasionally by a special canula (Drews-Smyth canula) and can have the following advantages over forewater membrane rupture:

1. In cases of poor engagement of the presenting part, hindwater rupture reduces the possibility of prolapse of the umbilical cord. This is the main indication for using a Drews-Smyth canula in clinical practice today, but these canulas are now rarely used because their rigid, curved shape have occasionally caused injury; it is suggested that the pliable, flexible probe of the present invention would make this procedure more safe.
2. In cases of good engagement of the presenting part, the membranes may be tightly applied to the skin (usually scalp) of the baby and a conventional amnlotomy hook may scratch the skin surface as the membranes are being ruptured. Sometimes, no amniotic fluid is obtained and there is uncertainty as to whether the membranes are still intact. These problems are avoided by rupture of the membranes above the presenting part where there is more amniotic fluid.

The access channel can then be left open to allow amniotic fluid to escape even when the presenting part would otherwise, due to a tight fit, be sealing the pelvic outlet; thus the presence of meconium would still be noted on inspection.

Another possible use for such an access channel is the insertion of an intrauterine pressure catheter or transducer. When, during labour, it becomes apparent that such a catheter needs to be inserted for pressure monitoring, and often distressing additional vaginal examination for this insertion can be avoided and the already in-situ probe of the present invention can be used to guide the tip of the catheter through it and around the presenting part up into the uterus. The additional cost of using a long pressure catheter is reserved for those cases where it becomes actually necessary as labour progresses, while the discomfort of and extra, intracervical digital examination is avoided. By taping the proximal ends of the pressure catheter and the probe of the present invention together, the balloon which is securing the probe in place also ensures that the pressure catheter does not slip out due to maternal movement or accidental pulling by an attendant.

BRIEF DESCRIPTION OF THE DRAWINGS

The present invention will now be described by way of example with reference to the accompanying drawings, in which:

FIG. 1 is a plan view of fetal probe according to this invention;

FIG. 2 is a side view of the probe shown in FIG. 1;

DETAILED DESCRIPTION OF THE DRAWINGS

Figure 3:
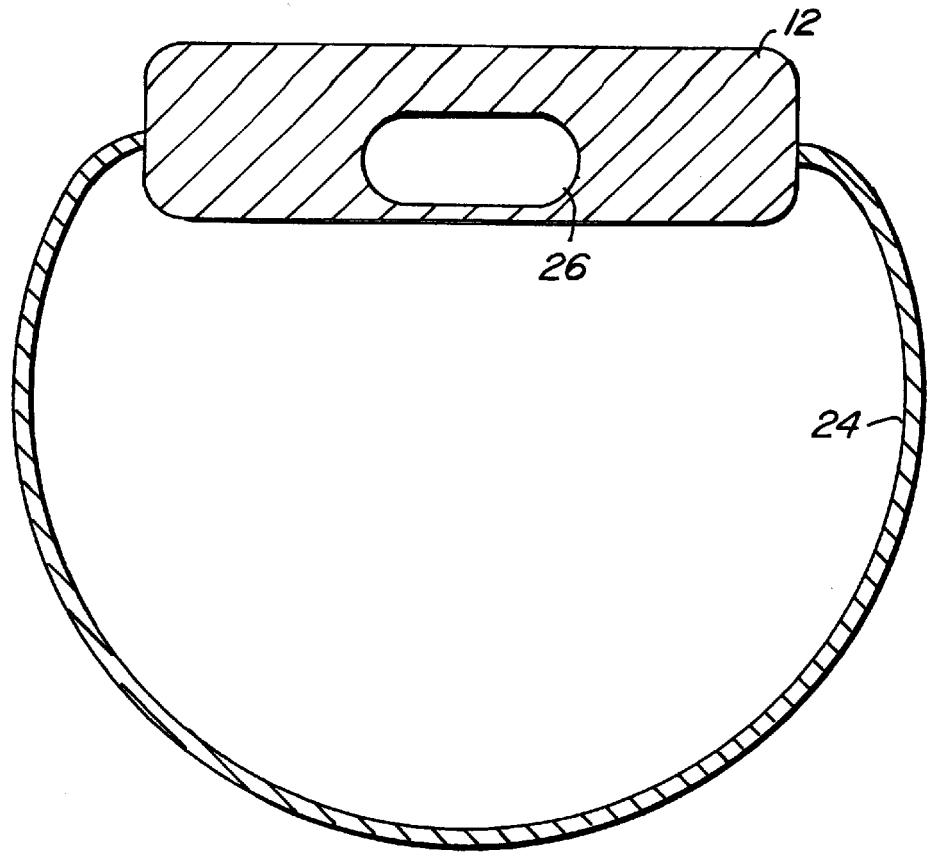
FIGS. 3, 4 and 5 are enlarged scale sections on respectively lines 3—3, 4—4, 5—5 of FIG. 2.

Referring initially to FIGS. 1 and 2, the probe 10 comprises a strip like body portion 12. This carries on one surface a maternal reference electrode 14 and, on the opposite surface and towards the distal end of the probe, fetal sensor means 16. In this example, the sensor means 16 takes the form of an ECG electrode 18, a photodiode 20 and a photosensor 22. In known fashion, the photodiode 20 and photosensor 22 can be used to determine the oxygenation levels of fetal blood. At the distal end of the body portion 12 is formed an inflatable balloon or sac 24. This sac is of generally hemi-spherical shape.

Figure 4:
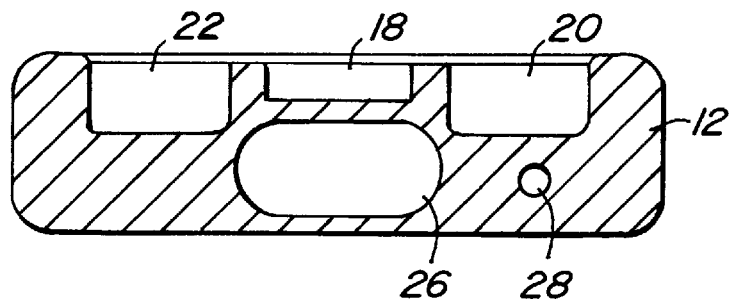
Figure 5:
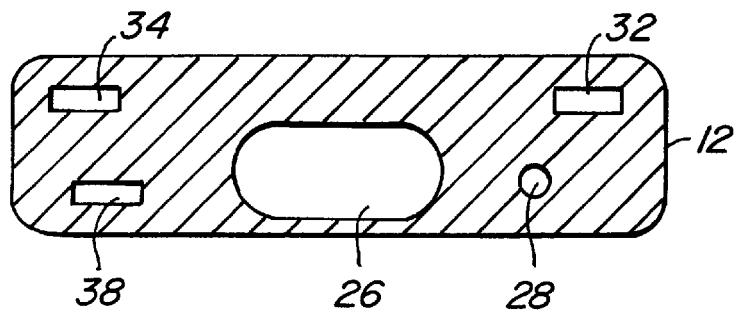

As seen more clearly in FIGS. 3, 4 and 5, a lozenge shaped channel 26 extends through the length of the body portion 12. The purpose of this channel 26 will be described in more detail later. A bore 28 in the probe body communicates between the inflatable sac 24 and a coupling 30 at the proximal end of the body portion. A syringe or other suitable means for inflating the sac 24 can in use be connected with this coupling 30. Passages 32 and 34 carry leads communicating between the external lead 36 and, respectively, the photodiode 20 and photosensor 22. Passage 36 similarly carries a lead connecting with the fetal electrode 18.

Figure 6:
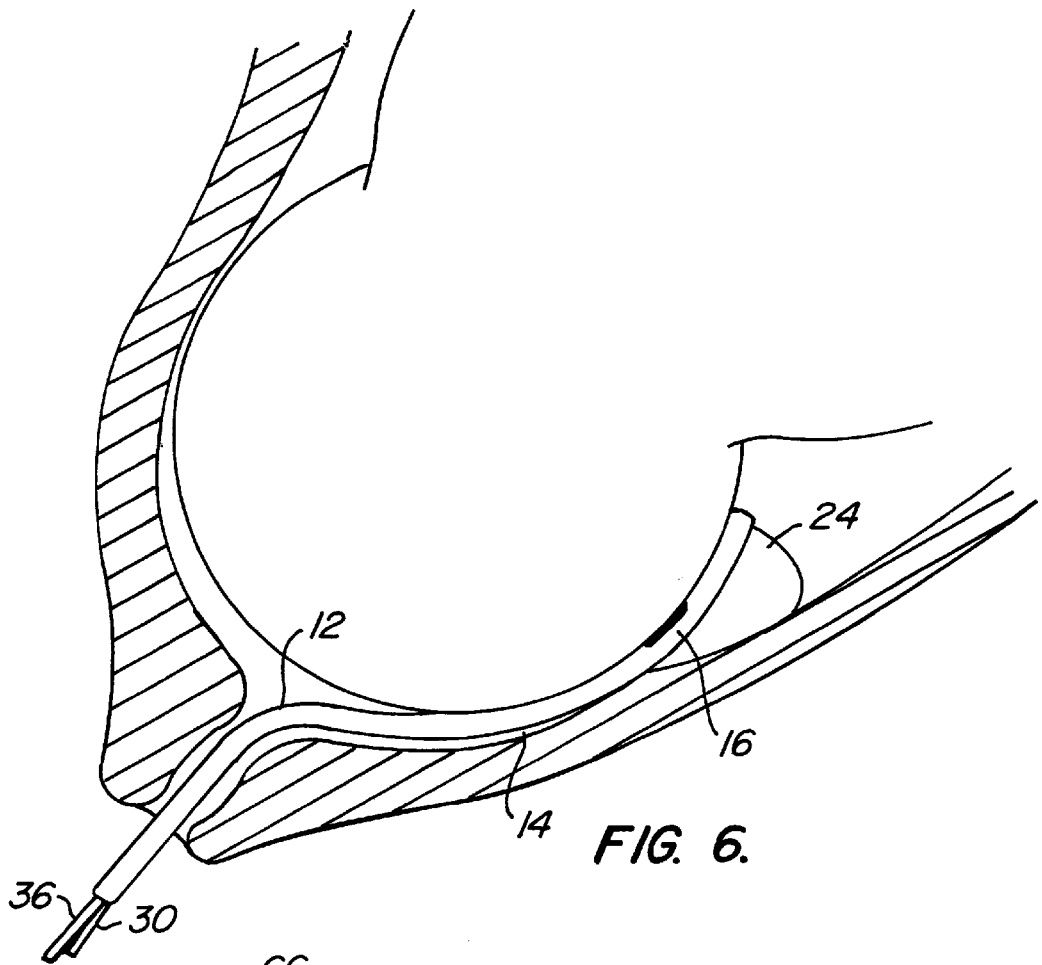
FIG. 6 is a diagrammatic representation of the probe of FIG. 1 when positioned in the uterus.

The intended manner of use of the described fetal probe can best be understood with reference to FIG. 6. The probe, with the sac 24 deflated, is introduced through the cervix passing between the presenting part of the fetus (which will usually be the fetal head) and the opposing uterine wall. When the probe has been inserted to a length of approximately 15 cm, the sac 24 is inflated. This will typically be achieved by the use of a syringe connected with coupling 30. Slight tension applied to the probe by the attendant will then ensure that the sensor is securely held against the fetal scalp with the inflated sac 24 wedged between the maternal tissues and the fetal head. It will be recognised that this wedging action will maintain the position of the fetal sensor even in the face of contraction of other maternal of fetal movements. Indeed, the probe should remain in position even if the parturient were to stand up and walk during labour.

With the sac 24 positioned to the maternal side of the probe body portion 12, and because of the shape of the sac being generally convex to the maternal tissues and flat toward the body portion, the effect is to urge the body portion and thus the fetal sensor into still closer contact with the fetal skin.

Because the probe according to this invention extends only a relatively short distance into the uterus, as compared for example with that disclosed in GB-A-2195897, it is not necessary for the amniotic membrane to be deliberately ruptured. Moreover, it is to be expected that proper usage of the probe according to this invention will generally not lead to rupture of the membrane. The avoidance of premature rupture of the amniotic membrane offers clinical advantages. By this criterion, the preferred insertable length of the probe body is from 10 to 20 cm and advantageously about 15 cm.

The channel 26 can be used, with the probe positioned as shown in FIG. 6, to pass appropriate instruments into the uterine cavity in a straightforward manner and with minimum discomfort to the parturient. The examples have already been quoted of the insertion of appropriate instruments for amniotomy, drainage of amniotic fluid and passage of an intrauterine pressure catheter.

Because of the nature of the probe and its sensor, it will not be harmful to the fetus and satisfactory signals will usually still be achieved whether the sensor is positioned on the fetal scalp or on the face or ears of the fetus.

The use of a generally flat body portion enables the correct opposition of the fetal and maternal electrodes respectively. An alternative tubular arrangement would be possible, however, which did not require insertion in a particular orientation. In that case, pairs of fetal electrodes (for example) and maternal electrodes would be provided at opposite sides of the probe. Signals would be taken from both electrodes of each pair and the associated circuitry would be arranged to select the fetal or maternal signals as appropriate.

In a modification (which is not shown in the drawings) the described hemi-spherical sac is replaced by a spherical sac positioned between two flat leaves formed integrally with the probe. Conveniently, the fetal sensor can be provided on one leaf and the maternal electrode on the other. During insertion of the probe the two leaves lie flat together, with the free end of one leaf being held for example in a small overhand at the end of the opposing leaf. By inflation of the sac, the two leaves can be forced apart to provide the desired wedging action.

Whilst the described inflatable sac or balloon represents the preferred arrangement, there are a variety of further location means which can be expanded remotely to serve the same wedging function. One such alternative location means will now be described with reference to FIG. 7 and 8. FIG.

7 shows the distal end of a tubular probe body portion 50. The tubular wall is bifurcated to form two hemi-cylindrical wall sections 52. The thickness of these wall sections 52 is significantly less than the wall thickness in the remainder of the body portion as shown for example at 54. The shoulder 56 between the wall sections 52 and 54 serves to define a hinge region about which the wall sections 52 can be splayed outwardly.

An expander 58 has a hollow stem 60 extending through the length of the body portion 50 and projects from the proximal end (not shown) of the probe to enable manipulation by the attendant. At the distal end, the expander 58 has an integral conical section 62 with a rounded forward surface 64. A bore 66 extends through the length of the expander 58 for the subsequent insertion of, for example, a trocular.

Figure 7:
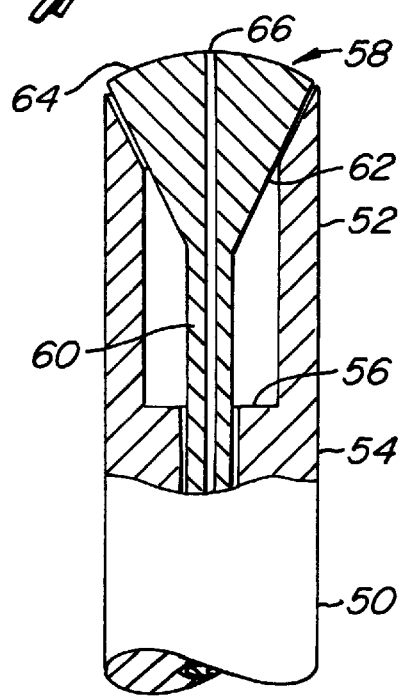
FIG. 7 is a part sectional view through the end of a fetal probe according to a further embodiment of this invention.
Figure 8:
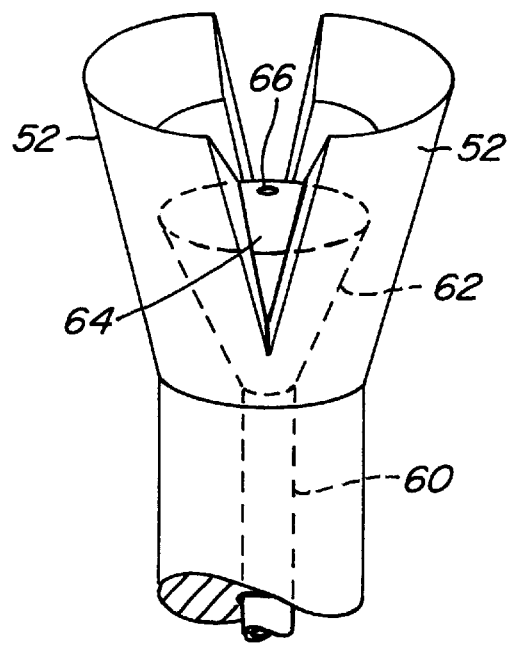
FIG. 8 is a sketch showing a different orientation of the probe end shown in FIG. 7.

The probe in inserted through the cervix in the orientation shown in FIG. 7. The rounded surface 64 facilitates entry of the probe and the wall sections 52 are held tightly closed through inherent resilience. Once the body portion 50 has been inserted to the appropriate length, the expander 60 is withdrawn relatively to the body portion 50. The effect of this relative motion, as depicted in FIG. 8 is to force the hemi-cylindrical wall sections 52 outwardly. In a manner analogous with the inflation of the previously described inflatable sac, this expansion of the distal end of the probe enables a wedging action between the presenting part of the fetus and the opposing maternal tissues.

Still other arrangements will occur to the skilled man in which integral wedging surfaces are urged outwardly on relative longitudinal movement between the body portion and an elongate, parallel expander passing through the body portion.

In appropriate circumstances, the fetal sensor may be held sufficiently firmly against the presenting part of the fetus without the need for additional locating means. This invention accordingly encompasses within its scope the use of a fetal probe which can be inserted between the presenting part of the fetus and the opposing maternal tissue without rupture of the amniotic membrane. In this form of the invention, the described access channel through the probe body remains of importance.

What is claimed is:

1. A fetal probe comprising a single elongate body portion having a fetal sensor mounted thereon, said body portion being constructed and arranged for insertion into the cervix and above the presenting part of the fetus whereby said fetal sensor is positioned between the fetus and the maternal tissue during cervical dilation, expandable means on a distal end of the body portion for urging said sensor into engagement with the fetus and having a collapsed state to facilitate insertion of the body portion into the cervix and above the presenting part of the fetus and an expanded state for urging the fetal sensor into close engagement with the fetus, the expandable means in its expanded state defining a surface having a portion displaced from the distal end of the body portion to wedge the probe between the fetus and the maternal tissue such that the probe is secured against removal without returning said expandable means to is unexpanded state and the sensor is urged into closer engagement with the fetus, said sensor also being urged into closer engagement with the fetus and the maternal tissue by intrauterine pressure during delivery, said expandable means being mounted on only said single electrode body portion.

2. A probe according to claim 1 wherein the expandable means comprises an inflatable member joined to said member and including a surface which is displaced from said member upon expansion.

3. A probe according to claim 2 wherein the expandable means includes an integral wedging surface urged outwardly from the body portion upon expansion.

4. A fetal probe according to claim 1 wherein the fetal sensor comprises in combination an ECG electrode and means for transcutaneous fetal oximetry.

5. The probe according to claim 1, wherein the expandable means comprises an inflatable balloon.

* * * * *

UNITED STATES PATENT AND TRADEMARK OFFICE
CERTIFICATE OF CORRECTION

PATENT NO. : 6,186,945 B1  
DATED : February 13, 2001  
INVENTOR(S) : Gardosi, Jason Otto It is certified that error appears in the above-identified patent and that said Letters Patent is hereby corrected as shown below:

Column 6, claim 1,
Line 25, should read -- single elongate body -- and not "single electrode body".

Signed and Sealed this

Twentieth Day of November, 2001

Attest:

*Nicholas P. Godici*

NICHOLAS P. GODICI
*Attesting Officer*   *Acting Director of the United States Patent and Trademark Office*